US012629349B2

(12) United States Patent
Okunishi et al.

(10) Patent No.: US 12,629,349 B2
(45) Date of Patent: May 19, 2026

(54) RECOGNITION ABILITY IMPROVING AGENT

(71) Applicant: Kinjirushi Co., Ltd., Nagoya (JP)

(72) Inventors: Isao Okunishi, Nagoya (JP); Tomoe Kato, Nagoya (JP)

(73) Assignee: Kinjirushi Co., Ltd., Nagoya (JP)

( * ) Notice: Subject to any disclaimer, the term of this patent is extended or adjusted under 35 U.S.C. 154(b) by 1012 days.

(21) Appl. No.: 16/965,252

(22) PCT Filed: Jan. 31, 2018

(86) PCT No.: PCT/JP2018/003245
§ 371 (c)(1),
(2) Date: Jul. 27, 2020

(87) PCT Pub. No.: WO2019/150497
PCT Pub. Date: Aug. 8, 2019

(65) Prior Publication Data
US 2021/0069146 A1     Mar. 11, 2021

(51) Int. Cl.
| | |
|---|---|
| A61K 31/26 | (2006.01) |
| A23L 2/52 | (2006.01) |
| A23L 33/00 | (2016.01) |
| A23L 33/105 | (2016.01) |
| A61K 9/00 | (2006.01) |
| A61K 36/31 | (2006.01) |
| A61P 25/00 | (2006.01) |

(52) U.S. Cl.
CPC ............... *A61K 31/26* (2013.01); *A23L 2/52* (2013.01); *A23L 33/105* (2016.08); *A23L 33/40* (2016.08); *A61K 9/0053* (2013.01); *A61K 9/0056* (2013.01); *A61K 9/0095* (2013.01); *A61K 36/31* (2013.01); *A61P 25/00* (2018.01); *A23V 2002/00* (2013.01)

(58) Field of Classification Search
None
See application file for complete search history.

(56) References Cited

FOREIGN PATENT DOCUMENTS

| | | | | |
|---|---|---|---|---|
| JP | 2007-509131 A | | 4/2007 | |
| JP | 2007-246404 A | | 9/2007 | |
| JP | 2009126826 A | * | 6/2009 | |
| JP | 2010001282 A | * | 1/2010 | |
| JP | 2010-184892 A | | 8/2010 | |
| JP | 2010280573 A | * | 12/2010 | .............. A61P 39/00 |
| WO | 2005037848 A2 | | 4/2005 | |
| WO | 2010/140271 A1 | | 12/2010 | |

OTHER PUBLICATIONS

JP2009126826A English Translation (Year: 2009).*
EESR in the counterpart European Application No. 18903772.4 dated Oct. 19, 2021.

Morroni, F. et al. "Neuroprotection by 6-(methylsulfinyl)hexyl isothiocyanate in a 6-hydroxydopamine mouse model of Parkinson's disease" Brain Research 1589 (2014) 93-104.
Sita, G. et al. "Isothiocyanates Are Promising Compounds against Oxidative Stress, Neuroinflammation and Cell Death that May Benefit Neurodegeneration in Parkinson's Disease" International Journal of Molecular Sciences (2016) 17(9) 1454.
International Preliminary Report on Patentability issued for PCT/JP2018/003245, dated Aug. 13, 2020.
First Office Action issued in the corresponding Chinese Patent Application No. 201880087397.9 with machine-generated English translation, dated Nov. 30, 2022.
Office Action in the counterpart Korean Application No. 10-2020-7025148 dated Nov. 1, 2021 and its machine English translation.
International Search Report issued for PCT/JP2018/003245, dated May 1, 2018.
Written Opinion of the International Searching Authority issued for PCT/JP2018/003245, dated May 1, 2018.
Final Rejection issued in the corresponding Indonesian Patent Application No. P00202006317 with English translation, dated Mar. 29, 2023.
Office Action issued for Indonesian patent application serial No. P00202006317, dated Jul. 20, 2021, with partial English translation.
Office Action issued in Chinese Patent Application No. 201880087397.9 dated Jul. 19, 2023 with English translation.
Noriaki, K. et al., "Antimicrobial Activities in Isothiocyanate Compounds", Department of Food and Lifestyle, Faculty of Food Culture, Kurashiki Sakuyo University, 1999, vol. 25, No. 1, 7-13, with English Abstract.
Akbaraly, N. et al., "Plasma Carotenoid Levels and Cognitive Performance in an Elderly Population: Results of the EVA Study", Journal of Gerontology: Medical Sciences, 2007, vol. 62A, No. 3, 308-316.
Office Action issued for EP patent application Serial No. 18903772.4, dated Nov. 17, 2023.
Office Action issued in the corresponding Chinese Patent Application No. 201880087397.9 with machine-generated English translation, dated Mar. 9, 2024.
Iris Blotenberg et. al.; "Towards a Process Model of Sustained Attention Tests." Journal of Intelligence, Department of Psychology, Philipps-University of Marburg, Gutenbergstr. 18, 35032 Marburg, Germany;(2019); 25 pages.
Richard J. Perry et. al.; "Attention and executive deficits in Alzheimer's disease." Brain (1999), 122, 383-404; 22 pages.
Martijn J. M. Lamers et. al.; "Role of Gestalt grouping in selective attention: Evidence from the Stroop task."; Perception & Psychophysics. 2007, 69 (8), 1305-1314; 10 pages.
The State of Queensland; "Attention and Concentration after Brain Injury" Fact Sheet; Aug. 2018; ABIOS Neuropsychologist; 3 pages.
Phoebe Zapanta Trio et. al.; "DNA Microarray Highlights Nrf2-Mediated Neuron Protection target by Wasabi-Derived Isothiocyanates in IMR-32 Cells." ; Libertas Academica. May 21, 2016. 10 73-83; 11 pages.

(Continued)

*Primary Examiner* — Adam C Milligan
*Assistant Examiner* — Jed A Kucharczk
(74) *Attorney, Agent, or Firm* — Westman, Champlin & Koehler, P.A.; Amanda M. Prose

(57) ABSTRACT

A recognition function improving agent according to the present disclosure includes 6-methylsulfinylhexyl isothiocyanate. The recognition function improving agent according to the present disclosure includes a wasabi extract.

7 Claims, No Drawings

(56)        References Cited

OTHER PUBLICATIONS

Notice of Reasons for Rejection for Chinese Patent Application No. 201880087397.9, dated May 25, 2024, with machine English translation.

Office Action for corresponding European Patent Application No. 18903772.4, issued Jul. 25, 2025.

"Guidance for Industry Estimating the Maximum Safe Starting Dose in Initial Clinical Trials for Therapeutics in Adult Healthy Volunteer", Jul. 1, 2005, US Department of Health and Human Services, Food and Drug Administration, Center for Drug Evaluation and Research, p. 1-30.

* cited by examiner

RECOGNITION ABILITY IMPROVING AGENT

CROSS-REFERENCE TO RELATED APPLICATION

This Application is a Section 371 National Stage Application of International Application No. PCT/JP2018/003245 filed Jan. 31, 2018 and published as WO 2019/150497 A1 on Aug. 8, 2019, in Japanese, the contents of which are hereby incorporated by reference in their entirety.

TECHNICAL FIELD

The present invention relates to a recognition function improving agent that improves a brain function, particularly a recognition function.

BACKGROUND ART

Improvement of learning abilities has been desired by a wide range of people from children to adults in various situations. Researches have been conducted on compositions that improve learning abilities (see Japanese Unexamined Patent Application Publication No. 2007-246404).

Examples of the brain function that improves learning abilities include a recognition function and an information processing ability.

For improving the learning abilities, the inventor diligently sought a new recognition function improving agent that improves the recognition function and the information processing ability.

It is desirable that one aspect of the present disclosure provides a new recognition function improving agent.

PRIOR ART DOCUMENT

Patent Document

Patent Document 1: Japanese Unexamined Patent Application Publication No. 2007-246404

SUMMARY OF THE INVENTION

One aspect of the present disclosure provides a recognition function improving agent comprising 6-methylsulfinylhexyl isothiocyanate.

Another aspect of the present disclosure provides a recognition function improving agent comprising a wasabi extract.

MODE FOR CARRYING OUT THE INVENTION

A recognition function improving agent according to an embodiment of the present disclosure comprises 6-methylsulfinylhexyl isothiocyanate (6-Methylsulfinyhexyl isothiocyanate) (6-MSITC for short).

6-MSITC used in the present disclosure can be obtained through a chemical synthesis method, but may be extracted and purified from plants. Examples of the plants include Bataceae (Bataceae), Brassicaceae (Brassicaceae), Bretschneideraceae (Bretschneideraceae), Capparaceae (Capparaceae), Caricaceae (Caricaceae), Euphorbiaceae (Euphorbiaceae), Gyrostemonaceae (Gyrostemonaceae), Limnanthaceae (Limnanthaceae), Moringaceae (Moringaceae), Pentadiplandraceae (Pentadiplandraceae), Phytolaccaceae (Phytolaccaceae), Pittosporaceae (Pittosporaceae), Resedaceae (Resedaceae), Salvadoraceae (Salvadoraceae), Tovariaceae (Tovariaceae), and Tropaeolaceae (Tropaeolaceae). Specifically, the examples of the plants include wasabi (*Wasabia japonica*) [also known as hon-wasabi], horseradish (*Armoracia rusticana*) [also known as yama-wasabi], *Batis maritima* (Japanese name unknown), mustard (*Brassica juncea*), broccoli (*Brassica oleracea* var. *italica*), mouse-ear cress (*Arabidopsis thaliana*), shepherd's purse (*Capsella bursa-pastoris*), watercress (*Nasturtium officinale*), *Bretschneidera sinensis* (Japanese name unknown), caper (*Capparis spinosa*), papaya (*Carica papaya*), *Drypetes roxburghii* (Japanese name unknown); *Putranjiva roxburghii* (Japanese name unknown), *Tersonia brevipes* (Japanese name unknown), *Limnanthes douglasii* (Japanese name unknown), horseradish tree (*Moringa oleifera*), *Pentadiplandra brazzeana* (Japanese name unknown), pokeweed (*Phytolacca americana*), *Bursaris spinose* var. *incana* (Japanese name unknown), white mignonette (*Reseda alba*), *Salvadora persica* (Japanese name unknown), *Tovaria pendula* (Japanese name unknown), and Indian cress (*Tropaeolum majus*). 6-MSITC that can be used in the present disclosure is not limited to 6-MSITCs obtained from the aforementioned plants, and all natural resources containing 6-MSITC can be used as raw materials.

Examples of a method for extracting and purifying 6-MSITC include a method for extracting 6-MSITC from wasabi and horseradish that are Brassicaceae plants. Details of the extraction method are published in the official gazette of Japanese Patent No. 3919489.

It is desirable that 6-MSITC is extracted from wasabi or synthesized. Specific description of a method for chemically synthesizing 6-MSITC is as follows.

The method by Kjaer et al. was followed in principle. (Kjaer et al., Acta Chem. Scand., 11, 1298, 1957). 6-chlorohexanol was refluxed with $CH_3$—SNa to obtain 6-methylthiohexanol. 6-methylthiohexanol was reacted with thionyl chloride ($SOCl_2$) to obtain 6-chlorohexyl methyl sulfide. Then, an amino group was introduced to 6-chlorohexyl methyl sulfide by phthalimide potassium salt using the Gabriel method to produce N-(6-methylthiohexyl)-phthalimide. To N-(6-methylthiohexyl)-phthalimide, hydrazine hydrate was added and refluxed so as to obtain 6-methylthiohexylamine. Then, thiocarbonyl chloride was reacted with 6-methylthiohexylamine to obtain 6-methylthiohexyl isothiocyanate.

Further, a methylthio group in the obtained 6-methylthiohexyl isothiocyanate was oxidized with m-chloroperbenzoic acid to obtain 6-methylsulfinylhexyl isothiocyanate (6-MSITC) (Morimitsu et. al., J. Biol. Chem., 277, 3456, 2002).

The wasabi extract may be used in the recognition function improving agent of the present disclosure. It is desirable that the wasabi extract contains 6-MSITC.

The dose of the recognition function improving agent of the present disclosure is determined in consideration of a patient's age, sex, weight, usage, dose, and so on. Examples of the usage include oral administration. In the case of oral administration, it is preferable that daily dose of 6-MSITC in the recognition function improving agent is 0.01 mg/day to 10 mg/day, more preferably 0.05 mg/day to 5.0 mg/day, and desirably 0.1 mg/day to 1 mg/day.

In a case where the wasabi extract is used as the recognition function improving agent, it is preferable that the wasabi extract is ingested such that the daily dose of 6-MSTIC in the wasabi extract becomes 0.01 mg/day to 10 mg/day.

The recognition function improving agent of the present disclosure may be contained in foods, cosmetics, quasi-drugs, or foods with functional claims/foods for specified health uses.

The foods according to the present disclosure may contain the recognition function improving agent. The cosmetics according to the present disclosure may contain the recognition function improving agent. The quasi-drugs according to the present disclosure may contain the recognition function improving agent.

The foods containing the recognition function improving agent of the present disclosure may be in any form and the form is not limited. Specific examples of the forms of the foods include general foods, general drinks, supplements, health foods, foods with health claims and foods for special dietary uses such as foods with functional claims and foods for specified health uses, soft drinks, tea drinks, health drinks, alcoholic beverages such as wines, confectioneries, cooked rices, breads, noodles, side dishes, and seasonings.

The cosmetics and the quasi-drugs containing the recognition function improving agent of the present disclosure may be in any form and the form is not limited. Specific examples of the cosmetics and the quasi-drugs include internal/external preparations, skin lotions, emulsions, creams, ointments, packs, skin cleansers, shampoos, hair conditioners, and bath additives.

Moreover, the dosage form of the cosmetics and the quasi-drugs containing the recognition function improving agent of the present disclosure is not limited. Specific examples of the dosage form of the cosmetics and the quasi-drugs include capsules, tablets, powders, granules, solutions, emulsions, creams, gels, ointments, sheets, and mousses.

To the recognition function improving agent of the present disclosure, in addition to 6-MSITC which is the main component, various optional components generally used for foods, cosmetics, and quasi-drugs may be added if necessary, as accessory components as long as the effects of the present disclosure are not impaired.

EXAMPLES

Following test substances were prepared, and the influence on brain function when the test substances were administered to humans was investigated.

(1) Preparation of Test Substances

The test substances are Sample 1 and Reference Sample 1. Sample 1 includes the wasabi extract with 6-MSITC, a cyclodextrin, gelatin, and a caramel coloring. The content of 6-MSITC in Sample 1 is 0.5 mg. Reference Sample 1 is identical to Sample 1 except that the wasabi extract is not contained. The form of Sample 1 and Reference Sample 1 is powder.

(2) Experiment

It is generally known that physical activities, such as exercises, are considered to improve a cognitive function and to inhibit impairment of cognitive function (Yasunaga A, Kimura K, Physical activity and cognitive function in the older Japanese adults, 25th Research-Aid Report, 2010: 129-13611, Yanagisawa H. et. al., Acute moderate exercise elicits increased dorsolateral prefrontal activation and improves cognitive performance with Stroop test., Neuroimage., 2010, 50(4): 1702-1710). It was also expected in the present example that having or not having an exercise habit would give an influence on various neuropsychological tests.

The test substances were given to test subjects without exercise habits, and the influence on brain functions was investigated. For the "test subjects without exercise habits", those who did not have regular exercises twice a week or more and 30 minutes or longer per time were determined to be the test subjects. The test substances were given to the test subjects, and the conditions of the test subjects were studied as described below. The test subjects are males and females aged 45 to 69 years without exercise habits. All the test subjects are aware of their forgetfulness, but are healthy individuals.

The test subjects who took the test substances were 37 subjects. The test subjects who took Sample 1 and Reference Sample 1, as the test substances, were respectively 19 subjects and 18 subjects. The test subjects who took Sample 1 were categorized into Group A (6-MSTIC intakers group). The test subjects who took Reference Sample 1 were categorized in Group P (6-MSTIC non-intakers group).

The test subjects were asked to take one tablet of Sample 1 or Reference Sample 1 per day at bedtime with cold or warm water. The duration of intake was eight weeks.

In human trial in which 0.2 to 1.0 mg of 6-MSTIC was given to humans, an antioxidant effect, a blood flow improving effect, an anti-inflammatory effect, and a skin condition improving effect have been reported (Kinjirushi Co., Ltd.). Accordingly, the content of 6-MSITC in Sample 1 was determined to be 0.5 mg.

The following tests were placed in the fourth week and the eighth week of intake.

(2-1) Stroop Test

Stroop test is a test to assess abilities to discriminate and process two different types of information (verbal information and color information) that simultaneously enter a brain. The test was conducted in accordance with the testing procedure of the new Stroop test (Hakoda Y, Watanabe M; New Stroop Test II, Toyo Physical Co.). This test consists of subtests of four steps ("Step 1", "2", "3", and "4") and, as the step advances, the level of difficulty increases. The test includes a plurality of problems. The test subjects solve the problems within a specified period of time. In each step, the number of achieved tasks, the number of correct answers, the number of incorrect answers (the number of errors), a reverse Stroop interference rate, and a Stroop interference rate were evaluated.

The number of achieved tasks means a processing speed to solve the problems. The number of correct answers is a numerical value corresponding to the number of problems that the test subject answered correctly. The number of incorrect answers is a numerical value corresponding to the number of problems that the test subject answered incorrectly. The reverse Stroop interference rate and the Stroop interference rate were respectively obtained by the following calculation formulae.

$$\text{Reverse Stroop interference rate (\%)} = 100 \times (\text{Number of correct answers in Step 1} - \text{Number of correct answers in Step 2})/\text{Number of correct answers in Step 1}$$

$$\text{Stroop interference rate (\%)} = 100 \times (\text{number of correct answers in Step 3} - \text{number of correct answers in Step 4})/\text{number of correct answers in Step 3}$$

An increase in the measured values of the number of achieved tasks and of the number of correct answers indicates an improvement. A decrease in the measured values of the number of incorrect answers (the number of errors), of the reverse Stroop interference rate, and of the Stroop interference rate indicates an improvement.

Step 1: to make a check mark for the color of the ink indicated by the word.

Step 2: The color indicated by the word and the color of the ink do not match. To make a check mark for the color of the ink indicated by the word.

Step 3: to select and make a check mark for the word that corresponds to the color of the ink.

Step 4: The color indicated by the word and the color of the ink do not match. To select and make a check mark for the word that corresponds to the color of the ink used to write the word.

Transitions of the measured values in Steps 1 to 4 and the amount of change since before intake in Steps 1 to 4 are shown: in Table 1 with regard to the numbers of achieved tasks; in Table 2 with regard to the numbers of correct answers; in Table 3 with regard to the numbers of incorrect answers; and in Table 4 with regard to the interference rates. In each table, "Measured value" shows actually measured values, and "Amount of change" is a value obtained by subtracting the numerical value before intake from the numerical value in the fourth week or the eighth week.

[Table 1]

TABLE 1

| | Stroop test (number of achieved tasks) [group of test subjects without exercise habits] | | | | |
|---|---|---|---|---|---|
| Item | Numerical value item | Group | Before intake | 4th week | 8th week |
| Step 1 | Measured value | P | 58.6 ± 7.1 | 60.2 ± 7.0 | 61.5 ± 7.2* |
| | | A | 58.7 ± 8.7 | 62.1 ± 7.8** | 64.4 ± 7.1** |
| | Amount of change | P | | 1.6 ± 5.1 | 2.9 ± 4.4 |
| | | A | | 3.4 ± 3.9 | 5.7 ± 3.4# |
| Step 2 | Measured value | P | 48.9 ± 5.2 | 51.6 ± 6.6* | 51.8 ± 7.5* |
| | | A | 52.2 ± 6.9 | 53.6 ± 7.3 | 55.5 ± 6.9** |
| | Amount of change | P | | 2.7 ± 4.1 | 2.8 ± 5.0 |
| | | A | | 1.4 ± 3.7 | 3.3 ± 3.1 |
| Step 3 | Measured value | P | 39.9 ± 5.2 | 40.8 ± 4.5 | 42.1 ± 5.0** |
| | | A | 40.5 ± 5.7 | 42.3 ± 6.1 | 43.2 ± 5.3** |
| | Amount of change | P | | 0.9 ± 2.8 | 2.1 ± 2.9 |
| | | A | | 1.8 ± 4.5 | 2.7 ± 3.9 |
| Step 4 | Measured value | P | 36.0 ± 5.2 | 36.9 ± 4.6 | 36.7 ± 7.0 |
| | | A | 36.5 ± 5.6 | 37.7 ± 6.4 | 40.6 ± 6.5** |
| | Amount of change | P | | 0.9 ± 2.6 | 0.7 ± 6.0 |
| | | A | | 1.3 ± 4.2 | 4.1 ± 2.9# |

All numerical values are shown as mean ± standard deviation.
Group P: n = 18,
Group A: n = 19
Intra-group comparison with before intake
*p < 0.05,
**p < 0.01 (1-sample t test)
Intergroup comparison with Group P
p < 0.05,
p < 0.01 (2-sample t test)
(Group A: 6-MSTIC intakers group, Group P: 6-MSTIC non-intakers group)

TABLE 2

| | Stroop test (number of correct answers) [group of test subjects without exercise habits] | | | | |
|---|---|---|---|---|---|
| Item | Numerical value item | Group | Before intake | 4th week | 8th week |
| Step 1 | Measured value | P | 58.6 ± 7.1 | 59.9 ± 7.1 | 61.4 ± 7.2* |
| | | A | 58.5 ± 8.7 | 62.1 ± 7.8** | 64.4 ± 7.1** |
| | Amount of change | P | | 1.3 ± 5.3 | 2.8 ± 4.3 |
| | | A | | 3.6 ± 4.0 | 5.8 ± 3.5# |
| Step 2 | Measured value | P | 48.8 ± 5.3 | 51.3 ± 6.7* | 51.5 ± 7.6* |
| | | A | 52.0 ± 7.1 | 53.4 ± 7.2 | 55.2 ± 6.8** |
| | Amount of change | P | | 2.5 ± 4.2 | 2.7 ± 5.1 |
| | | A | | 1.4 ± 3.7 | 3.2 ± 2.9 |
| Step 3 | Measured value | P | 39.9 ± 5.2 | 40.7 ± 4.4 | 41.8 ± 5.4* |
| | | A | 40.3 ± 5.6 | 42.3 ± 6.1 | 43.1 ± 5.4** |
| | Amount of change | P | | 0.8 ± 2.8 | 1.9 ± 3.1 |
| | | A | | 1.9 ± 4.5 | 2.7 ± 4.1 |
| Step 4 | Measured value | P | 35.9 ± 5.2 | 36.7 ± 4.6 | 36.6 ± 7.3 |
| | | A | 36.3 ± 5.6 | 37.6 ± 6.5 | 40.5 ± 6.6** |
| | Amount of change | P | | 0.8 ± 2.8 | 0.7 ± 6.3 |
| | | A | | 1.3 ± 4.1 | 4.2 ± 3.0# |

All numerical values are shown as mean ± standard deviation.
Group P: n = 18,
Group A: n = 19
Intra-group comparison with before intake
*p < 0.05,
**p < 0.01 (1-sample t test)
Intergroup comparison with Group P
p < 0.05,
p < 0.01 (2-sample t test)
(Group A: 6-MSTIC intakers group, Group P: 6-MSTIC non-intakers group)

TABLE 3

| | Stroop test (number of incorrect answers) [group of test subjects without exercise habits] | | | | |
|------|------------------------|-------|---------------|--------------|--------------|
| Item | Numerical value item | Group | Before intake | 4th week | 8th week |
| Step 1 | Measured value | P | 0.0 ± 0.0 | 0.2 ± 0.4* | 0.1 ± 0.2 |
| | | A | 0.2 ± 0.4 | 0.0 ± 0.0 | 0.0 ± 0.0 |
| | Amount of change | P | | 0.2 ± 0.4 | 0.1 ± 0.2 |
| | | A | | −0.2 ± 0.4 | −0.2 ± 0.4 |
| Step 2 | Measured value | P | 0.2 ± 0.4 | 0.3 ± 0.5 | 0.3 ± 0.5 |
| | | A | 0.2 ± 0.4 | 0.2 ± 0.4 | 0.3 ± 0.7 |
| | Amount of change | P | | 0.2 ± 0.6 | 0.1 ± 0.6 |
| | | A | | −0.1 ± 0.5 | 0.1 ± 0.9 |
| Step 3 | Measured value | P | 0.1 ± 0.2 | 0.1 ± 0.3 | 0.3 ± 0.6 |
| | | A | 0.2 ± 0.4 | 0.0 ± 0.0 | 0.1 ± 0.5 |
| | Amount of change | P | | 0.1 ± 0.4 | 0.2 ± 0.6 |
| | | A | | −0.2 ± 0.4 | −0.1 ± 0.6 |
| Step 4 | Measured value | P | 0.1 ± 0.5 | 0.2 ± 0.5 | 0.1 ± 0.5 |
| | | A | 0.2 ± 0.5 | 0.2 ± 0.4 | 0.1 ± 0.5 |
| | Amount of change | P | | 0.1 ± 0.5 | 0.0 ± 0.7 |
| | | A | | −0.1 ± 0.5 | −0.1 ± 0.3 |

All numerical values are shown as mean ± standard deviation.
Group P: n = 18,
Group A: n = 19
Intra-group comparison with before intake
*$p < 0.05$,
**$p < 0.01$ (1-sample t test)
Intergroup comparison with Group P
$p < 0.05$,
$p < 0.01$ (2-sample t test)
(Group A: 6-MSTIC intakers group, Group P: 6-MSTIC non-intakers group)

TABLE 4

| | Stroop test (interference rate) [group of test subjects without exercise habits] | | | | |
|------|------------------------|-------|----------------|-----------------|-----------------|
| Item | Numerical value item | Group | Before intake | 4th week | 8th week |
| Reverse Stroop interference rate | Measured value | P | 16.53 ± 4.64 | 14.37 ± 6.49 | 16.26 ± 7.01 |
| | | A | 10.88 ± 5.07 | 13.92 ± 5.89* | 14.16 ± 5.42* |
| | Amount of change | P | | −2.17 ± 8.25 | −0.27 ± 7.04 |
| | | A | | 3.04 ± 6.24# | 3.28 ± 5.24 |
| | Analysis of covariance | P | | 0.19 ± 1.59 | 1.13 ± 1.49 |
| | | A | | 0.81 ± 1.54 | 1.95 ± 1.44 |
| Stroop interference rate | Measured value | P | 9.84 ± 7.28 | 9.56 ± 8.31 | 12.39 ± 14.58 |
| | | A | 9.96 ± 7.30 | 10.90 ± 10.72 | 6.00 ± 9.56 |
| | Amount of change | P | | −0.28 ± 8.15 | 2.55 ± 14.34 |
| | | A | | 0.95 ± 11.82 | −3.96 ± 8.69 |

Numerical values of analysis of covariance in reverse Stroop interference rate are shown as mean ± standard error, and others are shown as mean ± standard deviation (unit = %).
Group P: n = 18,
Group A: n = 19
Intra-group comparison with before intake
*$p < 0.05$,
**$p < 0.01$ (1-sample t test)
Intergroup comparison with Group P
$p < 0.05$,
$p < 0.01$ (2-sample t test)
Minimum mean-square value of reverse Stroop interference rate before intake = 13.63%
(Group A: 6-MSTIC intakers group, Group P: 6-MSTIC non-intakers group)

The results of Stroop test will be explained.

(a) Number of Achieved Tasks

In Step 1, Group A (6-MSITC intakers group) showed a significant increase in the amount of change in the eighth week as compared with Group P (6-MSITC non-intakers group). Also in Step 4, Group A showed a significant increase in the amount of change in the eighth week as compared with Group P. In Steps 2 and 3, no significant intergroup difference was found in the amount of change at every test.

In intra-group comparisons where the before-intake value and the after-intake values are compared within each group, significant increases were respectively found: in Step 1, in the eighth week in Group P and in the fourth and eighth weeks in Group A; in Step 2, in the fourth and eighth weeks in Group P and in the eighth week in Group A; in Step 3, in the eighth week in the both groups; and in Step 4, in the eighth week only in Group A.

(b) Number of Correct Answers

In Step 1, the amount of change in the eighth week significantly increased in Group A as compared with Group P. In Step 4, the amount of change in the eighth week significantly increased in Group A as compared with Group P. In Steps 2 and 3, there was no significant intergroup difference in the amount of change at every test.

In intra-group comparisons where the before-intake value and the after-intake values are compared within each group, significant increases were respectively found: in Step 1, in the eighth week in Group P and in the fourth and eighth weeks in Group A; in Step 2, in the fourth and eighth weeks in Group P and in the eighth week in Group A; in Step 3, in the eighth week in the both groups, and in Step 4, in the eighth week only in Group A.

(c) Number of Incorrect Answers

In Step 1, the amount of change in the fourth week was 0.2±0.4 in Group P and –0.2±0.4 in Group A, and the amount of change in the eighth week was 0.1±0.2 in Group Research Foundation (no date). Purdue Peg-board Tes. Lafayette, Lafayette Instrument Co.). The present test was performed using Purdue Pegboard (A929-1, manufactured by SAKAI Medical Co., Ltd.) in accordance with the procedure manual, and reverse Stroop interference rates and Stroop interference rates were calculated. The test was performed once each for right hand, left hand, and both hands in this order. With regard to dominant hand, non-dominant hand, and both hands, the transition of the measured values and the amount of change since before intake are shown in Table 5. An increase in the measured values indicates an improvement.

TABLE 5

| Purdue pegboard test [group of test subjects without exercise habits] | | | | | |
|---|---|---|---|---|---|
| Item | Numerical value item | Group | Before intake | 4th week | 8th week |
| Dominant hand | Measured value | P | 12.9 ± 1.7 | 13.6 ± 1.7 | 13.9 ± 1.1* |
| | | A | 13.1 ± 2.0 | 13.4 ± 2.0 | 14.1 ± 1.9* |
| | Amount of change | P | | 0.6 ± 2.0 | 0.9 ± 1.7 |
| | | A | | 0.4 ± 1.6 | 1.0 ± 1.7 |
| Non-dominant hand | Measured value | P | 12.4 ± 1.6 | 12.7 ± 1.4 | 12.8 ± 1.2 |
| | | A | 12.8 ± 1.6 | 13.3 ± 1.5 | 13.5 ± 2.3* |
| | Amount of change | P | | 0.2 ± 1.6 | 0.4 ± 1.8 |
| | | A | | 0.5 ± 1.1 | 0.7 ± 1.4 |
| Both hands | Measured value | P | 10.1 ± 1.1 | 10.4 ± 1.4 | 10.7 ± 1.2* |
| | | A | 10.5 ± 1.7 | 11.2 ± 1.3* | 10.9 ± 1.7 |
| | Amount of change | P | | 0.4 ± 1.2 | 0.6 ± 1.2 |
| | | A | | 0.7 ± 1.3 | 0.5 ± 1.4 |

All numerical values are shown as mean ± standard deviation (unit: point).
Group P: n = 18,
Group A: n = 19
Intra-group comparison with before intake
*p < 0.05,
**p < 0.01 (1-sample t test)
Intergroup comparison with Group P
p < 0.05,
p < 0.01 (2-sample t test)
(Group A: 6-MSTIC intakers group, Group P: 6-MSTIC non-intakers group)

P and –0.2±0.4 in Group A. In Steps 2, 3, and 4, there was no significant intergroup difference in the amount of change at every test.

In intra-group comparisons where the before-intake value and the after-intake values are compared within each group, a significant increase was found, in Step 1, in the fourth week only in Group P. In other items, no significant change was found in both groups.

(d) Interference Rates

With regard to the reverse Stroop interference rates, the amount of change in the fourth week was significantly small in numerical value in Group P as compared with Group A. Since the before-intake value was significantly small in Group A as compared with Group P, analysis of covariance was performed in which the before-intake value was used as the covariate. As a result, no significant intergroup difference was observed between Group P and Group A. With regard to the Stroop interference rates, no significant intergroup difference was found in the amount of change in the fourth week.

In intra-group comparisons where the before-intake value and the after-intake values are compared within each group, the reverse Stroop interference rate significantly increased in the fourth and eighth weeks only in Group A. No significant change in the Stroop interference rates was found in both groups.

(2-2) Purdue Pegboard Test

Purdue pegboard test is a test for assessing dexterity in manual work such as assembling and packing (Purdue The results of Purdue pegboard test will be explained.

With regard to all the items, no significant difference between Group A and Group P was found in the amount of change at every test. In intra-group comparisons between the before-intakes value and the after-intake values, significant increases were found in the eighth week in the both groups in the test using dominant hands, in the eighth week only in Group A in the test using non-dominant hands, and in the eighth week in Group P and in the fourth week in Group A in the test using both hands.

(2-3) RAVLT (Ray Auditory Verbal Learning Test)

RAVLT (Lezak M. D., Neuropsychological Assessment, 2005, Sozo-Shuppan) is a test for assessing capacities of immediate and short-term memories, and retention and reproduction abilities of such memories. Semantically-unrelated 15 words (List A) were auditorily presented, and, immediately following this, the test subject was asked to repeat these words. The same procedure was run five times (first trial to fifth trial). Subsequently, the test subject was asked to repeat another 15 words (List B) that were different from those in List A in the same manner. Then, the test subject was asked to verbally recall the words from List A that the test subject could still remember (sixth trial: memory after an interference task). Furthermore, the following tests (2) to (5) were conducted as interference tasks, and 20 minutes later, the test subject was asked to verbally recall the words from List A that the test subject could still remember (seventh trial: delayed reproduction).

To assess memory input, short-term memory was evaluated from the number of achieved tasks STM (Short Term Memory) in the first trial. To assess learning process and function including a memory capacity and a state of mental exhaustion, a total immediate memory was evaluated using the total TIM (Total Immediate Memory) of the number of achieved tasks in the first trial to the fifth trial. The verbal learning ability was evaluated using a value VLA (Verbal Learning Ability) obtained by subtracting the number of achieved tasks in the first trial from the number of achieved tasks in the fifth trial. Using a value RI (Retroactive Interference Effect: Retroactive Interference Effect) obtained by subtracting the number of achieved tasks in the sixth trial from the number of achieved tasks in the fifth trial and dividing the difference by the number of achieved tasks in the fifth trial, how much memory of a previously learnt material was lost by a newly learnt material, or how much remembering of the previously learnt material was interfered was evaluated. Moreover, using a difference obtained by subtracting the number of achieved tasks in the sixth trial from the number of achieved tasks in the seventh trial, how much memory was lost after a short period of time was evaluated. Regarding the number of achieved tasks in each trial, STM, TIM, VLA, and the difference between the seventh trial and the sixth trial, an increase in the measured values indicates an improvement. Regarding RI, a decrease in the measured values indicates an improvement.

With regard to the first to the seventh trials, List B, STM, TIM, VLA, RI, and the difference between the seventh trial and the sixth trial, the transitions of the measured values and the amount of change since before intake are shown in Table 6 and Table 7.

TABLE 6

| RAVLT (Ray Auditory Verbal Learning Test) [group of test subjects without exercise habits] −1 | | | | | |
|---|---|---|---|---|---|
| Item | Numerical value item | Group | Before intake | 4th week | 8 th week |
| 1st trial | Measured value | P | 4.6 ± 1.2 | 6.5± 1.3** | 8.3 ± 2.3** |
| | | A | 4.6 ± 1.2 | 5.8 ± 1.1** | 8.2 ±= 1.9** |
| | Amount of change | P | | 1.9 ± 1.6 | 3.7 ± 2.3 |
| | | A | | 1.2 ± 1.3 | 3.5 ± 1.8 |
| 2nd trial | Measured value | P | 7.8 ± 1.7 | 8.8 ± 2.0* | 10.1 ± 2.3** |
| | | A | 6.6 ± 1.1 | 8.7 ± 1.7** | 10.1 ± 1.5** |
| | Amount of change | P | | 1.0 ± 1.8 | 2.3 ± 2.2 |
| | | A | | 2.2 ± 1.6# | 3.5 ± 1.4 |
| | Analysis of covariance | P | | 1.2 ± 0.4 | 2.6 ± 0.4 |
| | | A | | 1.9 ± 0.4 | 3.3 ± 0.4 |
| 3rd trial | Measured value | P | 8.6 ± 1.8 | 10.4 ± 1.9** | 11.2 ± 2.0** |
| | | A | 8.3 ± 1.1 | 9.9 ± 1.5** | 10.9 ± 1.3** |
| | Amount of change | P | | 1.8 ± 2.0 | 2.6 ± 1.9 |
| | | A | | 1.6 ± 1.7 | 2.6 ± 1.7 |
| 4th trial | Measured value | P | 9.6 ± 2.1 | 11.1 ± 1.7** | 11.9 ± 2.0** |
| | | A | 9.4 ± 1.0 | 10.5 ± 1.6** | 11.8 ± 1.3** |
| | Amount of change | P | | 1.5 ± 1.7 | 2.3 ± 2.1 |
| | | A | | 1.1 ± 1.6 | 2.4 ± 1.8 |
| 5th trial | Measured value | P | 10.8 ± 1.7 | 11.7 ± 1.7** | 12.6 ± 1.9** |
| | | A | 10.9 ± 1.4 | 11.4 ± 1.9 | 11.7 ± 1.3* |
| | Amount of change | P | | 0.8 ± 1.2 | 1.8 ± 1.3 |
| | | A | | 0.5 ± 1.6 | 0.8 ± 1.7 |
| 6th trial (memory after interference task) | Measured value | P | 8.4 ± 1.7 | 9.7 ± 2.6** | 11.7 ± 2.3** |
| | | A | 8.5 ± 2.2 | 9.8 ± 2.1* | 11.1 ± 2.1** |
| | Amount of change | P | | 1.3 ± 1.7 | 3.3 ± 2.1 |
| | | A | | 1.3 ± 2.2 | 2.6 ± 2.0 |
| 7th trial (20 minutes delayed reproduction) | Measured value | P | 7.7 ± 2.9 | 8.9 ± 3.2** | 11.3 ± 2.9** |
| | | A | 7.7 ± 2.2 | 9.2 ± 2.7** | 11.1 ± 1.8** |
| | Amount of change | P | | 1.2 ± 1.5 | 3.6 ± 2.5 |
| | | A | | 1.4 ± 1.7 | 3.4 ± 1.7 |

Numerical values of analysis of covariance in 2nd trial are shown as mean ± standard error, and others are shown as mean ± standard deviation (unit: piece).
Group P: n = 18,
Group A: n = 19
Intra-group comparison with before intake
*p < 0.05,
**p < 0.01 (1-sample t test)
Intergroup comparison with Group P
p < 0.05,
p < 0.01 (2-sample t test)
Minimum mean-square value of 2nd trial before intake = 72 pieces
(Group A: 6-MSTIC intakers group, Group P: 6-MSTIC non-intakers group)

TABLE 7

| RAVLT (Ray Auditory Verbal Learning Test) [group of test subjects without exercise habits] − 2 | | | | | | |
|---|---|---|---|---|---|---|
| Item | Unit | Numerical value item | Group | Before intake | 4th week | 8th week |
| List B (interference task) | Piece | Measured value | P | 4.3 ± 0.9 | 4.7 ± 1.8 | 4.7 ± 1.4 |
| | | | A | 4.6 ± 1.4 | 4.1 ± 1.1 | 4.3 ± 1.0 |
| | | Amount of change | P | | 0.4 ± 1.6 | 0.4 ± 1.4 |
| | | | A | | −0.5 ± 1.6 | −0.3 ± 1.7 |
| STM | Piece | Measured value | P | 4.6 ± 1.2 | 6.5 ± 1.3** | 8.3 ± 2.3** |
| | | | A | 4.6 ± 1.2 | 5.8 ± 1.1** | 8.2 ± 1.9** |

TABLE 7-continued

| Item | Unit | Numerical value item | Group | Before intake | 4th week | 8th week |
|---|---|---|---|---|---|---|
| | | Amount of change | P | | 1.9 ± 1.6 | 3.7 ± 2.3 |
| | | | A | | 1.2 ± 1.3 | 3.5 ± 1.8 |
| TIM | Piece | Measured value | P | 41.4 ± 6.7 | 48.4 ± 7.4** | 54.1 ± 9.4** |
| | | | A | 39.8 ± 4.1 | 46.5 ± 6.2** | 52.7 ± 5.2** |
| | | Amount of change | P | | 7.1 ± 4.5 | 12.7 ± 7.2 |
| | | | A | | 6.6 ± 5.2 | 12.9 ± 5.8 |
| VLA | Piece | Measured value | P | 6.2 ± 1.7 | 5.2 ± 1.4* | 4.3 ± 1.9** |
| | | | A | 6.3 ± 1.4 | 5.6 ± 1.5 | 3.6 ± 1.9** |
| | | Amount of change | P | | −1.1 ± 2.0 | −1.9 ± 2.5 |
| | | | A | | −0.7 ± 1.7 | −2.7 ± 1.8 |
| RI | % | Measured value | P | 0.22 ± 0.13 | 0.17 ± 0.16 | 0.08 ± 0.11** |
| | | | A | 0.22 ± 0.16 | 0.14 ± 0.12 | 0.05 ± 0.16** |
| | | Amount of change | P | | −0.05 ± 0.16 | −0.15 ± 0.16 |
| | | | A | | −0.08 ± 0.16 | −0.17 ± 0.14 |
| 7th trial - | Piece | Measured value | P | −0.7 ± 2.1 | −0.8 ± 2.1 | −0.4 ± 1.7 |
| 6th trial | | | A | −0.8 ± 1.5 | −0.6 ± 1.5 | 0.0 ± 1.2* |
| | | Amount of change | P | | −0.2 ± 1.8 | 0.3 ± 2.1 |
| | | | A | | 0.2 ± 1.6 | 0.8 ± 1.4 |

RAVLT (Ray Auditory Verbal Learning Test) [group of test subjects without exercise habits] − 2

All numerical values are shown as mean ± standard deviation.
Group P: n = 18,
Group A: n = 19
Intra-group comparison with before intake
*$p < 0.05$,
**$p < 0.01$ (1-sample t test)
Intergroup comparison with Group P
$p < 0.05$,
$p < 0.01$ (2-sample t test)
(Group A: 6-MSTIC intakers group, Group P: 6-MSTIC non-intakers group)

The results of RAVLT will be explained.

In any of the items, there was no significant intergroup difference in the amount of change in the eighth week.

In the second trial, the change of amount in the fourth week significantly increased in Group A as compared with Group P (Group P 1.0±1.8 pieces, Group A 2.2±1.6 pieces). Since the before-intake value was significantly small in Group A as compared with Group P, analysis of covariance was performed in which the before-intake value was used as the covariate. As a result, no significant intergroup difference was observed between Group P and Group A.

In intra-group comparisons where the before-intake value and the after-intake values are compared within each group, significant increases were found in the fourth and eighth weeks in the both groups with regard to the first, second, third, fourth, sixth, and seventh trials, STM, and TIM. With regard to List B, there was no significant change in the both groups. With regard to the fifth trial, significant increases were found in the fourth and eighth weeks in Group P and in the eighth week in Group A. With regard to VLA, significant decreases were found in the fourth and eighth weeks in Group P and in the eighth week in Group A. With regard to RI, significant decreases were found in the eighth week in the both groups. With regard to the difference between the seventh trial and the sixth trial, a significant increase was found in the eighth week only in Group A.

(3) Discussion

In Stroop test, significant increases in the amount of change were found in the eighth week in Group A (6-MSITC intakers group) as compared with Group P (6-MSITC non-intakers group) with regard to "Number of achieved tasks" and "Number of correct answers" in Steps 1 and 4.

With regard also to "Number of incorrect answers" in Step 3, a significant improvement was observed in Group A as compared with Group P. Although there was no significant intergroup difference in the amount of change in the eighth week, the number of incorrect answers decreased in Group A as compared with Group P.

It is considered that Stroop test can measure both attentional function and information processing speed, and the improvements in "Number of achieved tasks" and "Number of correct answers" in Steps 1 and 4 of Stroop test indicates that, if food containing 6-MSITC is given to middle-aged and old-aged male and female individuals who do not have daily exercise habits and are aware of their forgetfulness, the discrimination and processing abilities (attentional function), which is part of the cognitive function, are likely to improve. Although a clear definition is not yet established, the cognitive function is known to include various functions such as a memory function, verbal, behavioral, visual and visual space cognitive, attentional, performing functions, decision making, face expression and emotional responses (Yamauchi T et al., Handbook of Mental and Psychological Function Assessment, Nakayama Shoten Co., Ltd, 2015). In particular, the attention function is regarded as important in assessing the cognitive function, since the attentional function is not a single function but closely supports learning, memory, performing functions and activities of a working memory (Shinozaki K, Tsuji T, Psychiatric Disorder and Cognitive Function, Shinkoh Igaku Shuppansha Co., Ltd., 2009:55-61). Previous researches have reported that a cognitive decline with aging is more likely to occur in tasks that require attention and information processing speed (Chodzko-Zajko W J. and Moore K. A., Physical Fitness and Cognitive Functioning in Aging, Exercise and Sport Sciences Reviews, 1994, 22(1):195-200, Hawkins H. L., Kramer A. F. and Capaldi D., Aging, exercise, and attention, Psychology and Aging, 1992, 7(4):643-653). Considering these past researches, it can be said that it is an important finding that an attentional function improving effect of food containing 6-MSITC is indicated in the present experiment.

Many parts of the mechanism of action of 6-MSITC remain unknown. 6-MSITC is considered to have the antioxidant effect and the anti-inflammatory effect due to depressed production of active oxygen, and an anti-platelet aggregation effect, improvements in blood flow and blood circulation in blood vessels, and so on have been also reported (Kinae N, Furugori M, Kojima M, All about Wawabi, Gakkai Shuppan Center, 2006). It is possible that these effects of 6-MSITC inhibit cell damages, thereby contributing to improve functions of a central nervous system. The anti-platelet aggregation effect was studied using human platelets, and it has been reported that 6-MSITC contained in the wasabi extract shows aggregation inhibitory activity which is about 20 times as strong as that of aspirin. Regarding the efficacy of the wasabi extract on blood flow, it has been reported that, as a result of ingestion of 5 g of hon-wasabi by humans, the period of time required for 100 µL of blood to flow was shortened, and thus an improvement in blood flow was observed (Kinae N, Furugori M, Kojima M, All about Wasabi, Gakkai Shuppan Center, 2006). From these findings, it is likely that ingestion of food containing 6-MSITC improved blood flow due to the anti-platelet aggregation effect, reducing low oxygen state and ischemic state in the brain, providing the effect of reducing cell damages caused by active oxygen and the like due to the antioxidant effect associated with the reduced production of active oxygen, and contributing to improve the cognitive function.

Particularly, the Stroop test showed remarkable difference (intergroup difference) between the 6-MSITC intakers group (Group A) and the 6-MSITC non-intakers group (Group P). This indicates that the discrimination and processing abilities which are part of the recognition function are likely to be improved.

In contrast, intergroup differences were barely observed in Purdue pegboard test and RAVLT. The pegboard is to assess dexterity in manual work, while RAVLT is a test for assessing capacities of the immediate and short-term memories, and the retention and reproduction abilities of such memories. In the experiment of the present example, improvements in a simple work ability and a memory ability were barely found as a result of ingesting 6-MSITC, but it was found out that the attentional function and the information processing speed were improved, that is, workings of more advanced level of brain functions were improved.

The invention claimed is:

1. A method for improving an information processing function of a subject in need of improving an information processing function, the method comprising:
  orally administering 6-methylsulfinylhexyl isothiocyanate to the subject at a dose of 0.05 mg/day to 5 mg/day.

2. The method according to claim 1, wherein the 6-methylsulfinylhexyl isothiocyanate is a component of an extract obtained from wasabi or a synthetic.

3. The method according to claim 1, wherein the 6-methylsulfinylhexyl isothiocyanate is contained in a food or a drink.

4. The method according to claim 3, wherein the 6-methylsulfinylhexyl isothiocyanate is contained in a food with a functional claim or a food for a specified health use.

5. The method according to claim 3, wherein the 6-methylsulfinylhexyl isothiocyanate is contained in a health drink.

6. The method according to claim 1, wherein the 6-methylsulfinylhexyl isothiocyanate is contained in a quasi-drug.

7. The method according to claim 1, wherein the information processing function is language information and color vision information processing function.

* * * * *